United States Patent
Shifrin et al.

(10) Patent No.: US 7,678,124 B2
(45) Date of Patent: Mar. 16, 2010

(54) SUPPLEMENTARY VASCULAR CLAMP FOR THE TOOL KIT OF AN OPEN APPROACH STAPLER

(75) Inventors: Edward G. Shifrin, 64 Ha-Shahar Street, Raanana (IL) 43565; Gennady S. Nickelshpur, Haifa (IL); Mordehy D. Shvartsman, Haifa (IL); Mark A. Umansky, Haifa (IL)

(73) Assignee: Edward G. Shifrin (IL)

( * ) Notice: Subject to any disclaimer, the term of this patent is extended or adjusted under 35 U.S.C. 154(b) by 1180 days.

(21) Appl. No.: 10/550,159

(22) PCT Filed: Feb. 19, 2004

(86) PCT No.: PCT/IL2004/000156

§ 371 (c)(1),
(2), (4) Date: Sep. 20, 2005

(87) PCT Pub. No.: WO2004/082723

PCT Pub. Date: Sep. 30, 2004

(65) Prior Publication Data

US 2006/0184197 A1    Aug. 17, 2006

(30) Foreign Application Priority Data

Mar. 23, 2003 (IL) .................................. 155038
Sep. 25, 2003 (IL) .................................. 158106

(51) Int. Cl.
*A61B 17/28* (2006.01)

(52) U.S. Cl. ........................................ 606/157

(58) Field of Classification Search ............. 606/48–52, 606/139–144, 151, 157, 205–210
See application file for complete search history.

(56) References Cited

U.S. PATENT DOCUMENTS 3,503,398 A   3/1970   Fogarty et al. ............... 128/346

(Continued)

FOREIGN PATENT DOCUMENTS

CA          1103119        6/1981    ................. 128/118

*Primary Examiner*—Kevin T Truong
(74) *Attorney, Agent, or Firm*—Ostrolenk Faber LLP

(57) ABSTRACT

The present invention relates to medicine, in particular, to clamps used in vascular surgery for occlusion of blood vessels during a surgical operation, such as vascular clamps used in aortic aneurysm repair. The claimed supplementary vascular clamp comprises a pair of pivoting arms, each of them having a proximal end and a distal handle end. Each pivoting arm contains clamping jaws rigidly attached to a respective proximal end of this arm and shaped as a concave semi-cylindrical or semi-oval cavity. The clamping jaws are movable between the open position and closed position and define a through cylindrical or oval cavity in their closed position. The clamping jaws of the vascular clamp are also provided with a tightening means to provide intra-aortal bending of the ends of staples of an open approach stapler. The tightening means is shaped as plates or a strip of resilient material. The strip may be provided with a tensioning device. The vascular clamp may be also provided with a compensating means for correcting non-uniformity in the thickness of aorta walls. The vascular clamp may be further provided with a compensating means for correction of irregularity in wall thickness of the aorta, a first and a second sealing means for providing secure enclosure of aorta walls, as well as a means for providing regular ejection of staples.

10 Claims, 6 Drawing Sheets

U.S. PATENT DOCUMENTS

| | | | |
|---|---|---|---|
| 4,531,519 A | 7/1985 | Dunn et al. | 128/327 |
| 5,236,437 A | 8/1993 | Wilk et al. | 606/207 |
| 5,282,812 A | 2/1994 | Suarez, Jr. | 606/158 |
| 5,391,181 A * | 2/1995 | Johnson et al. | 606/207 |
| 5,624,454 A | 4/1997 | Palti et al. | 606/151 |
| 5,921,996 A * | 7/1999 | Sherman | 606/157 |
| 6,187,003 B1 * | 2/2001 | Buysse et al. | 606/49 |
| 6,911,032 B2 * | 6/2005 | Jugenheimer et al. | 606/142 |

\* cited by examiner

US 7,678,124 B2

SUPPLEMENTARY VASCULAR CLAMP FOR THE TOOL KIT OF AN OPEN APPROACH STAPLER

CROSS REFERENCE TO RELATED APPLICATIONS

The present application is a 35 U.S.C. §371 national phase conversion of International Application No. PCT/IL2004/000156 filed Feb. 19, 2004, which claims priority from Israel patent application No. 155038 filed Mar. 23, 2003 and Israel Patent application No. 158106 filed Sep. 25, 2003, incorporated herein by reference.

BACKGROUND OF THE INVENTION

1. Field of the Invention

The present invention relates to medicine, particularly to clamps used in vascular surgery for occlusion of blood vessels during a surgical operation, such as vascular clamps used in aortic aneurysm repair.

2. Background of the Invention

Vascular clamps are very important in performing operations on blood vessels. Most often they serve for occlusion of a blood vessel by their jaws or other working members, which allows to temporarily stop the blood flow in the operated portion of this blood vessel. So, there are known vascular clamps disclosed in U.S. Pat. Nos. 4,531,519; 5,152,770; 5,282,812.

Dunn and Scarrow in U.S. Pat. No. 4,531,519 disclose a vascular clamp in the form of a tapering, flexible and tubular envelope which is wound around the blood vessel to be occluded and is inflated by air or another fluid.

Bengmark and Persson in U.S. Pat. No. 5,152,770 describe a similar device, which includes a flexible, elongate strip covered on its one side with a plurality of communicating bulbs. The strip is wound around the blood vessel or duct to be occluded and the bulbs are inflated to a pressure serving to occlude the duct. After deflation of the bulbs the strip is removed to allow the duct to re-open. As in previous vascular clamp, the application of the strip or envelope by winding it around the blood vessel and subsequently inflating it until the flow of blood or other body fluid is stopped, is a difficult and time consuming task. For this reason both devices are used in exceptional cases only.

Suarez in U.S. Pat. No. 5,282,812 discloses a vascular clamp in the form of a strip of metal bent into V-shape with its inside surfaces lined with a resilient material. Closing of a vessel is described, whereby the clamp is to be held in a forceps, to be pushed over the vessel to be occluded and pressed onto the vessel, whereupon the forceps is removed. The material of the strip is supposed to keep its shape after removal of the forceps and to maintain the necessary pressure during the operation. The device is provided with means for engaging the forceps jaws after completed surgery for opening the V and for removing the clamp. It is claimed that the strip material would have a positional memory for exerting the necessary pressure after positioning. This would require a different size and material of the device for every size of vessel and blood pressure.

Most of the known vascular clamps have two intersecting arms mounted on a common pivot and provided with clamping jaws at their first ends, as well as with fixing grips at their second ends. Among these are vascular clamps described in Canadian Pat. 1103119 and U.S. Pat. No. 5,624,454.

Muermans and Rivlin in Canadian Patent 1103119 disclose a surgical clamp having two clamping jaws and comprising a soft pad placed over each jaw. Each pad includes two cavities, one of them tightly located over the respective jaw, the second cavity is filled with a fluid or solid and is subsequently sealed. It is claimed that the device clamps the vessel without damage.

Devices described in U.S. Pat. Nos. 3,503,398 and 5,236,437 also have soft members on the inner surface of their clamping jaws to prevent damaging of blood vessel surface. These soft members are adapted to be filled with liquid or gas, see U.S. Pat. No. 5,236,437.

All aforesaid devices serve to cut off a portion of the blood vessel during a surgical operation to prevent the flow of blood over this portion.

Closest to the claimed invention is the "Padded vascular clamp" described in U.S. Pat. No. 5,624,454. Palti and Schnall in U.S. Pat. No. 5,624,454 disclose a vascular clamp for occluding a blood vessel or duct in a human or animal. The vascular clamp includes a pair of pivoting arms with a clamping jaw rigidly attached to a distal end of each pivoting arm. A concave substantially semi-cylindrical chamber is formed in each clamping jaw. The clamping jaws are movable between an open position and a closed position, and are aligned so as to form a substantially cylindrical chamber in the closed position. A balloon is mounted in the concave semi-cylindrical chamber of each clamping jaw. Each balloon includes a substantially semi-cylindrical rigid shell conforming to the concave semi-cylindrical chamber and a thin, elastic material pre-filled with a liquid or gaseous fluid at a predetermined pressure. The balloons are configured to completely surround and occlude the blood vessel or duct in the closed position of the vascular clamp. The rigid shell of each balloon is attached to its associated clamping jaw.

The distinction of this vascular clamp is that its design allows to adjust within a wide range the rate of occlusion of a blood vessel—from simple occlusion of this blood vessel to a complete closure of its lumen.

The suggested vascular clamp has a function different from that of known vascular clamps. It serves to clamp the outer surface of a blood vessel during a surgical operation when a special endovascular stapler for suturing a prosthesis—graft or stent-graft to the wall of a blood vessel, substantially the aorta, in direction from inside to outside via metal staples, is inserted within the blood vessel. Thus the development of the suggested vascular clamp pursues other goals.

An object of the present invention is to provide intra-aortal bending of the ends of staples emerging from an open approach endovascular stapler during a surgical procedure for suturing a prosthesis—graft or stent-graft to the wall of a blood vessel, substantially the aorta.

Another object of the present invention is a secure enclosure of aorta walls by clamping jaws of the claimed vascular clamp to close the possible clearance between the inner surface of clamping jaws and outer surface of the aorta, and prevent at the same time damage of the outer surface of the aorta walls.

Still another object of the present invention is a correction of irregularity in thickness of the aorta walls when applying the claimed vascular clamp.

SUMMARY OF THE INVENTION

The subject-matter of the present invention is a supplementary vascular clamp for the tool kit of an open approach stapler serving to occlude a blood vessel around this open approach stapler at the moment of its operation.

The vascular clamp according to the first and second embodiments comprises: a) a pair of rotatable levers, b) tightening means for providing intra-aortal bending of staple ends, c) fastener means for attaching the tightening means to a corresponding clamping jaw, and d) compensating means for correcting the irregularity in the thickness of aorta walls.

In the claimed vascular clamp each of the rotatable levers has a proximal end and a distal handle hand. Each rotatable lever contains clamping jaws rigidly attached to a corresponding proximal end of this lever and shaped as a concave semi-cylindrical cavity. The clamping jaws are adapted to move between an open position and a closed position, defining a through cylindrical cavity in closed position.

The rotatable levers intersect and are connected via a pivot pin at the point of intersection, near their proximal ends. These rotatable levers contain fixing grips near their distal handle ends.

Each clamping jaw of the vascular clamp is shaped as a concave semi-oval cavity having a concave inner surface and bent outer surface, substantially parallel with its inner surface. The clamping jaws are adapted to be rigidly attached to the proximal ends of rotatable levers of conventional vascular clamps.

The vascular clamp also has a tightening means for intra-aortal bending of staple ends of the open approach stapler and for securely enclosing the aorta walls via clamping jaws. The clamping means contains at least two plates of resilient material substantially rubber or plastic, and each of them is attached to the inner semi-cylindrical surface of a corresponding clamping jaw. To this end the vascular clamp is provided with fastener means for attaching the tightening means to corresponding clamping jaws.

In another embodiment the tightening means contains at least one strip of resilient material, substantially rubber or plastic, which is rigidly attached by each of its ends to the inner semi-cylindrical surface of a corresponding clamping jaw.

And finally, the tightening means may be formed as at least one strip of resilient material, substantially rubber or plastic, which is adapted to adjust the force of occluding the outer surface of a blood vessel. For this purpose the vascular clamp is provided with a mechanism for tensioning this strip.

The vascular clamp also has a compensating means for correcting irregularity in the thickness of aorta walls. It contains substantially a ridge at the free end of one of the clamping jaws and a valley opposite to this ridge at the corresponding free end of the second clamping jaw.

A vascular clamp according to the third embodiment comprises: a pair of rotatable levers, compensating means for correcting the irregularity in the thickness of aorta walls, a first tightening means for securely enclosing the aorta walls via clamping jaws, a second tightening means for securely enclosing the aorta walls via clamping jaws and, at last, a means for providing regular ejection of staples over the entire surface of clamping jaws.

In the claimed vascular clamp each of the rotatable levers has a proximal end and a distal handle end. Each rotatable lever contains clamping jaws rigidly attached to a corresponding proximal end of this lever and shaped as a concave semi-cylindrical cavity. The clamping jaws are adapted to move between an open position and a closed position, defining a through oval cavity in closed position.

The rotatable levers intersect and are connected via a pivot pin at the point of intersection, near their proximal ends. These rotatable levers contain fixing grips near their distal handle ends.

Each clamping jaw of the vascular clamp is shaped as a concave semi-oval cavity having a concave inner surface and a bent outer surface. The clamping jaws are adapted to be rigidly attached to the proximal ends of rotatable levers of conventional vascular clamps.

The compensating means for correcting irregularity in the thickness of aorta walls contains clamping jaws with concave semi-oval inner surfaces. The clamping jaws are configured to move between the open position and the closed position, defining in closed position a through oval cavity with the long axis of symmetry coinciding with the parting plane of these clamping jaws.

The first tightening means for secure enclosure of aorta walls contains clamping jaws shaped as concave semi-oval cavities. These clamping jaws overlap one another by their ends in such a way that the ends of one of the clamping jaws are female, and the ends of the other clamping jaws—male.

The second tightening means for secure enclosure of aorta walls contains clamping jaws the ends whereof facing and overlapping one another are flexible.

The means for providing regular ejection of staples over the whole inner surface of prosthesis connection with the aorta contains clamping jaws shaped as concave semi-oval cavities, the ends whereof facing and overlapping one another are disposed with a clearance between them.

The means for providing regular ejection of staples over the whole inner surface of prosthesis connection with the aorta contains clamping jaws shaped as concave semi-oval cavities the ends whereof facing and overlapping one another are disposed with a clearance of 0.3 mm between them.

BRIEF DESCRIPTION OF THE DRAWINGS

The invention will now be described in conjunction with the following drawings in which like reference numerals designate like elements and wherein.

DETAILED DESCRIPTION OF THE DRAWINGS

Figure 1:
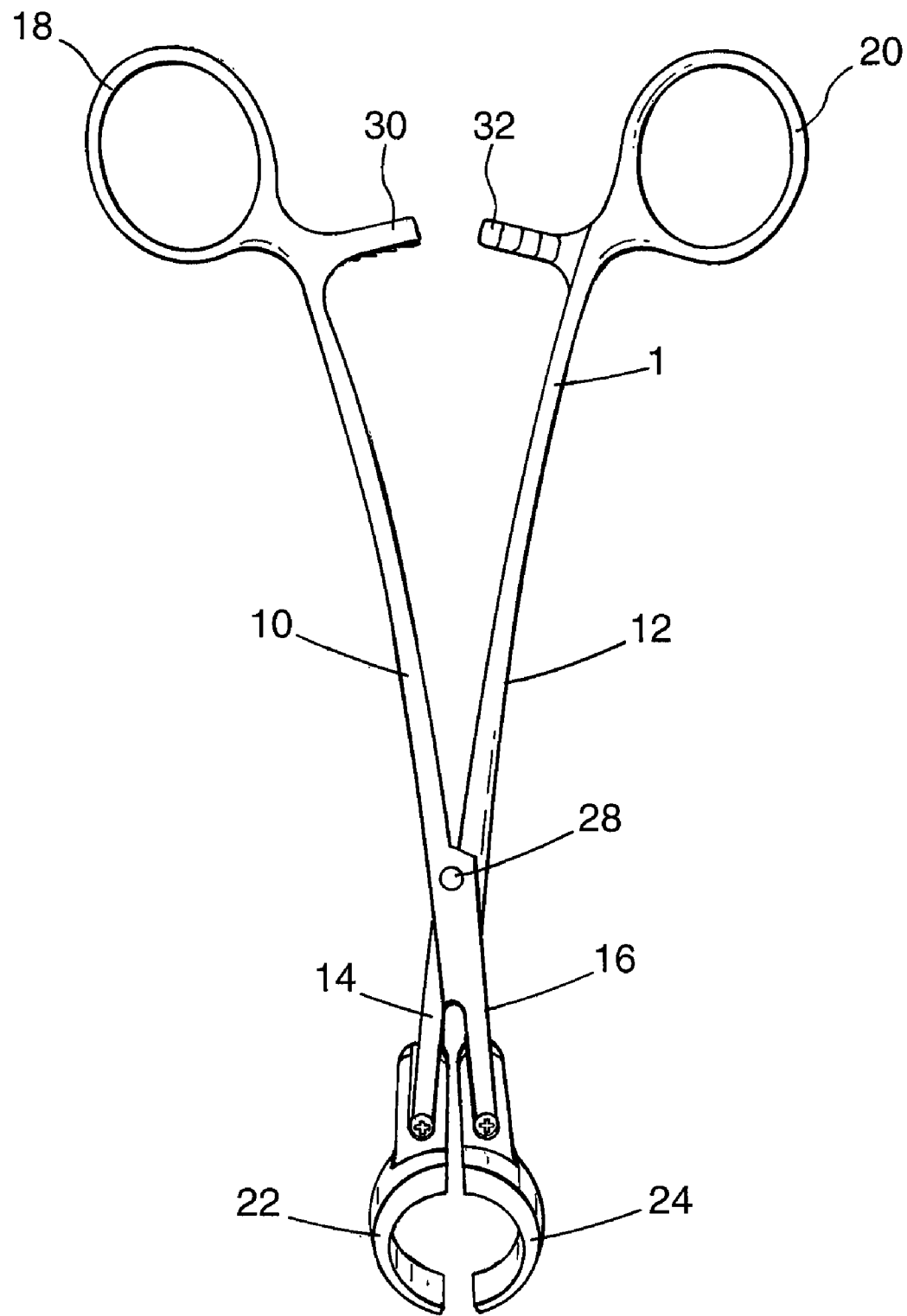
FIG. 1 is a perspective view of a supplementary vascular clamp according to the first embodiment of the present invention.

The preferred embodiments of the present invention are described below. The inventors of the present subject matter contemplate that the embodiments described herein are capable of use in the repair of other vessels and in other procedures. Thus, it is intended that the present invention cover the modifications and variations of the invention, provided they come within the scope of the appended claims and their equivalents.

The most preferred embodiments of a supplementary vascular clamp, according to the present invention, are shown in drawing FIGS. 1-14. The first and second embodiments of a supplementary vascular clamp, according to the present invention, are shown in drawing FIGS. 1-5, and the third embodiment is shown in drawing FIGS. 6-14.

The suggested supplementary vascular clamp 1 (FIG. 1) according to the first and second embodiments contains a pair of rotatable levers 10 and 12. Each rotatable lever 10 and 12 has a proximal end, 14 and 16 respectively, and a distal handle end, 18 and 20 respectively. Each rotatable lever contains clamping jaws, 22 and 24 respectively, rigidly attached to a corresponding proximal end, 14 and 16 of this lever 10 and 12 and shaped as a concave semi-cylindrical cavity. Clamping jaws 22 and 24 are movable between the open position (FIG. 1) and closed position (FIG. 2). Clamping jaws 22 and 24 define in closed position a through cylindrical cavity 26 (FIG. 2).

Figure 2:
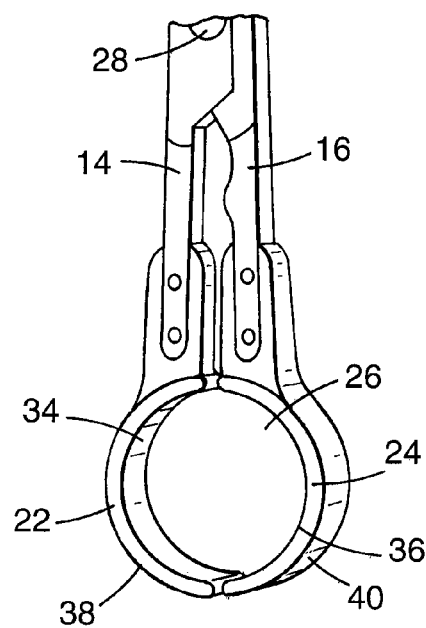
FIG. 2 shows the working part of the suggested vascular clamp in closed position.

Rotatable levers 10 and 12 intersect and are connected via a pivot pin 28 at their intersection point, near their proximal ends 14 and 16 (FIGS. 1, 2). Rotatable levers 10 and 12 contain fixing grips 30 and 32 near their distal handle ends 18 and 20 (FIG. 1).

Each clamping jaw 22 and 24 of vascular clamp 1 (FIG. 2) is shaped as a concave semi-cylindrical cavity having a concave inner surface, 34 and 36 respectively, and a bent outer surface, 38 and 40 respectively, substantially parallel with its inner surface 34 and 36. Clamping jaws 22 and 24 are adapted to be rigidly attached to proximal ends 14 and 16 of rotatable levers 10 and 12 of conventional clamps (FIGS. 1, 2).

Figure 3:
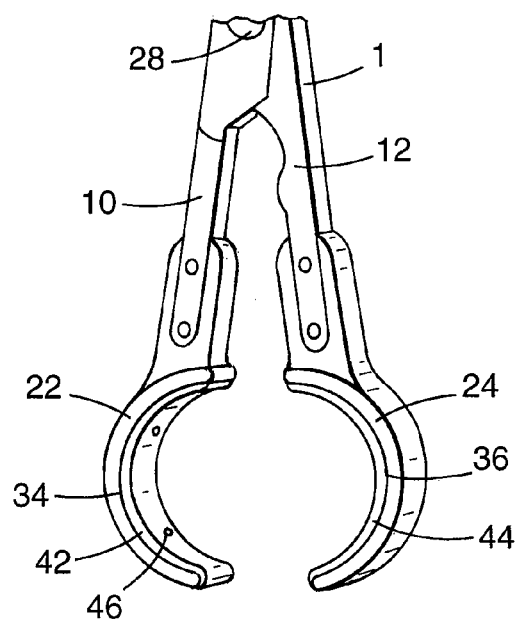
FIG. 3 shows a general view of the working part of the suggested vascular clamp according to its first embodiment.

Vascular clamp 1 also has a tightening means for intra-aortal bending of staples of the open approach stapler and secure enclosure of aorta walls via clamping jaws 22 and 24 (FIG. 3). The tightening means contains at least two plates from a resilient material, substantially rubber or plastic, 42 and 44 respectively, each of them being attached to the inner semi-cylindrical surface 34 and 36 of a corresponding clamping jaw 22 and 24. For this purpose vascular clamp 1 is provided with fastener means for connection of plates 42, 44 of the tightening means with a corresponding clamping jaw 22 or 24. These fastener means may be, for instance, screws 46 (FIG. 3). The fastener means may be as well glue layers or adhesive means.

Figure 4:
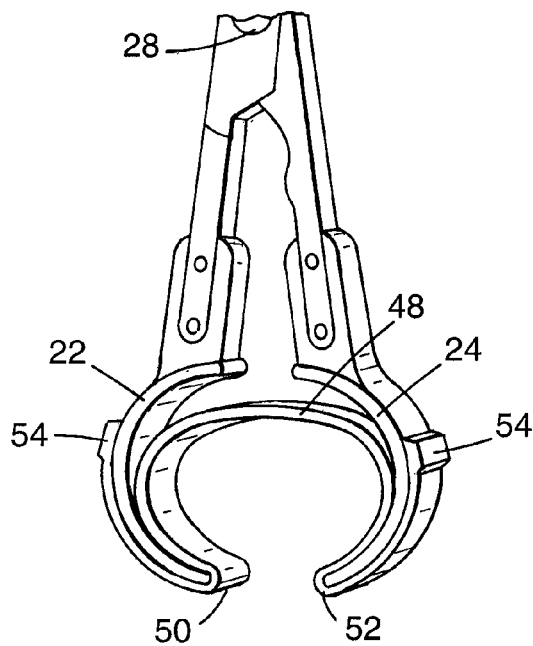
FIG. 4 shows a general view of the working part of the suggested vascular clamp according to its second embodiment.

The tightening means may as well contain at least one strip 48 from resilient material, substantially rubber or plastic (FIG. 4). This strip 48 is rigidly attached by each of its ends 50 and 52 to the inner semi-cylindrical surface 34 and 36 of a corresponding clamping jaw 22 and 24.

At last, the tightening means may contain at least one strip 48 from resilient material, substantially rubber or plastic, capable of adjusting the occlusion force of a blood vessel surface. For this purpose strip ends 50 and 52 may be lengthened to come onto bent outer surfaces 38 and 40 of clamping jaws 22 and 24, and vascular clamp 1 is provided with a mechanism for tensioning this strip containing one or two conventional tensioning devices 54 attached to one or two outer surfaces 38, 40 (FIG. 4).

Figure 5:
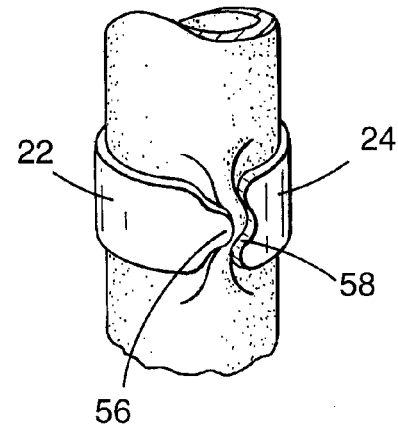
FIG. 5 shows the free end of the working part of the suggested vascular clamp provided with a compensating means.

The vascular clamp may also have a compensating means for correcting the irregularity in thickness of the walls of the aorta or other blood vessel. It substantially contains a ridge 56 at the free end of each clamping jaw, such as jaw 22, and valley 58 opposite to this ridge at a corresponding free end of second clamping jaw 24 (FIG. 5).

The claimed device according to the first and second embodiments operates as follows.

In a surgical operation, the aorta or some other blood vessel is exposed. Within the blood vessel there is inserted a prosthesis such as graft or stent-graft, and a means for securing this prosthesis to the blood vessel wall, such as an open approach stapler. Then a supplementary vascular clamp 1 is applied onto the outer surface of this blood vessel. At the moment of applying vascular clamp 1 its proximal ends 14 and 16 with clamping jaws 22 and 24 are located on both sides of the operated blood vessel, whereupon, due to forces applied to distal handle ends 18 and 20, levers 10 and 12 turn about pin 28 to bring together clamping jaws 22 and 24. Clamping jaws 22 and 24 define in their closed position a through cylindrical cavity 26 enclosing the blood vessel. Every effort is made to position supplementary vascular clamp 1 in such a way that it should be located by its clamping jaws 22 and 24 concentrically on the actuator of open approach stapler in the area of ejecting its staples. Then the position of clamp 1 is fixated by fixing grips 30 and 32, selecting such a position of their mutual connection, which provides sufficiently tight occlusion of the outer surface of blood vessel by clamping jaws 22 and 24.

Then the open approach stapler is actuated to suture by staples the prosthesis to the inner surface of blood vessel (not shown in the drawings). At the moment of the open approach stapler operation the tightening means of supplementary vascular clamp 1 containing plates 42, 44 or strip 48 tightly encloses the outer surface of blood vessel to prevent the surface from injuries and simultaneously provide the predetermined bending of staple ends of the stapler. The compensating means containing a ridge 56 and valley 58 at the ends of clamping jaws 22 and 24 provides correction of irregularity in thickness of walls of an operated blood vessel, in particular, the aorta.

Figure 6:
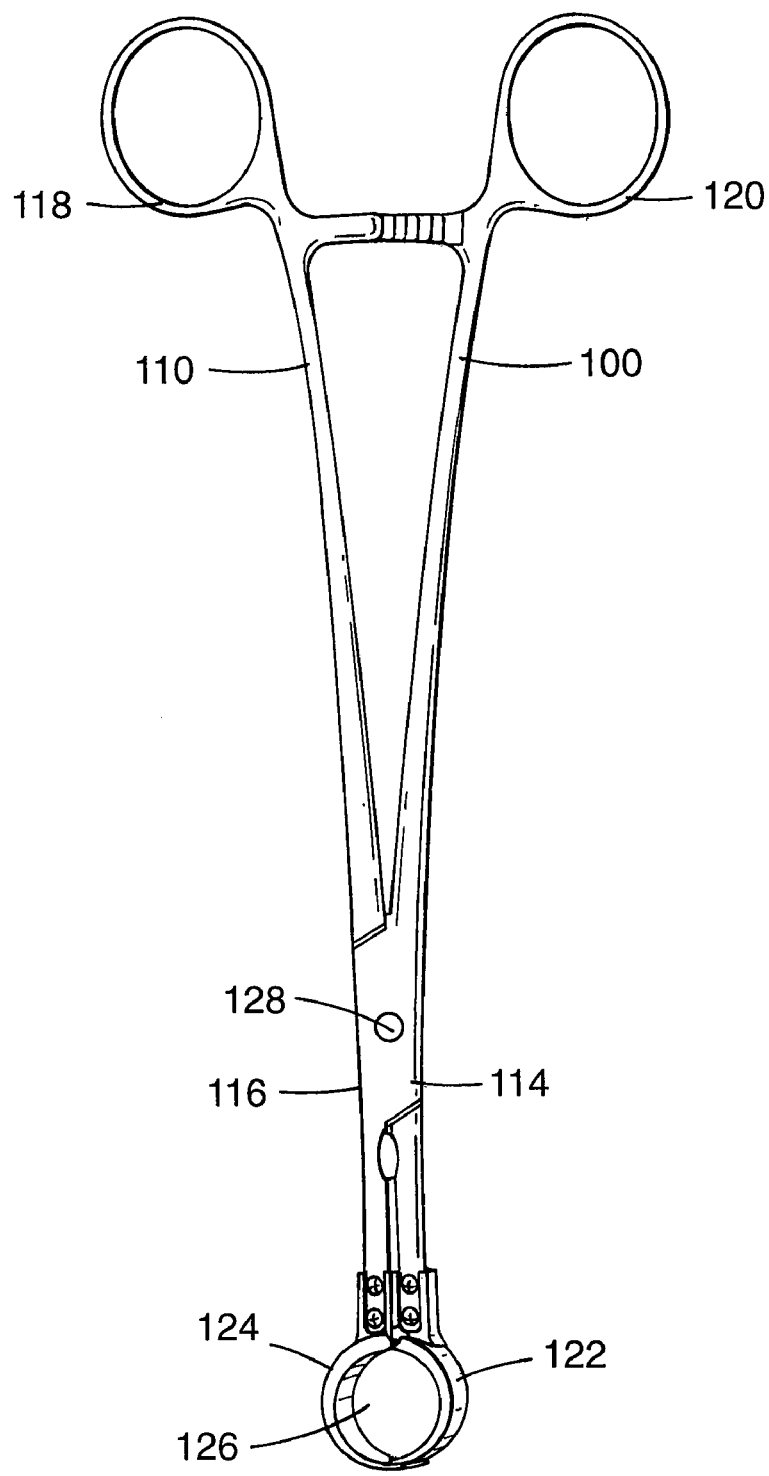
FIG. 6 is a perspective view of a supplementary vascular clamp according to the third embodiment of the present invention.

The suggested supplementary clamp 100 (FIG. 6) according to the third embodiment comprises a pair of rotatable levers 110 and 112. Each rotatable lever 110 and 112 has a proximal end, 114 and 116 respectively, and a distal handle end, 118 and 120 respectively. Each rotatable lever contains a clamping jaw, 122 and 124 respectively, rigidly attached to a corresponding proximal end, 114 or 116 of this lever 110 or 112 and shaped as a concave semi-oval cavity. Clamping jaws 122 and 124 are movable between open position (FIG. 13) and closed position (FIG. 6). Clamping jaws 122 and 124 define in closed position a through oval cavity 126 (FIG. 6).

Figure 7:
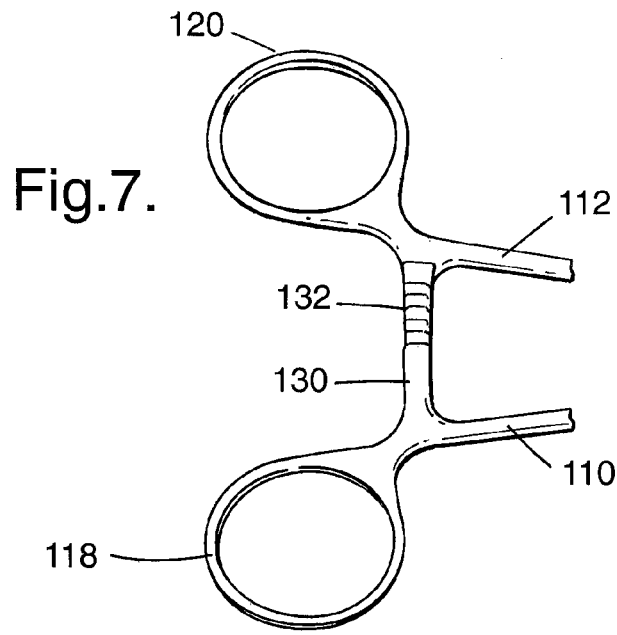
FIG. 7 shows the distal handle ends of rotatable levers with fixing grips.

Rotatable levers 110 and 112 intersect and are connected via a pivot pin 128 at their intersection point, near their proximal ends 114 and 116 (FIG. 6). Rotatable levers 110 and 112 contain fixing grips 130 and 132 near their distal handle ends 118 and 120 (FIG. 7).

Figure 8:
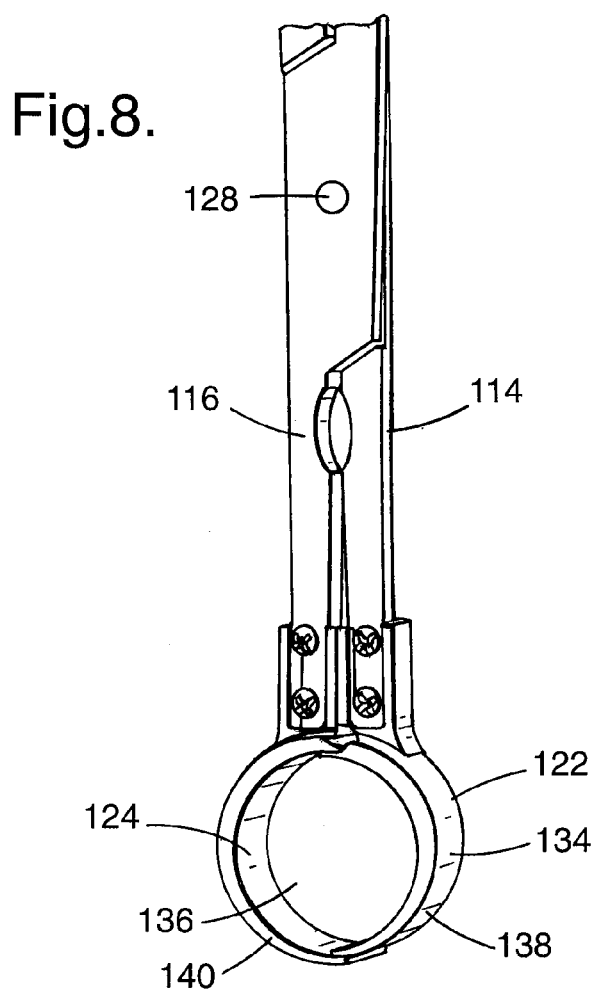
FIGS. 8, 9 show the working part of the suggested vascular clamp in closed position.

Each clamping jaw 122 and 124 of vascular clamp 100 (FIG. 8) is shaped as a concave semi-oval cavity having a concave inner surface, 134 and 136 respectively, and bent outer surface, 138 and 140 respectively. Clamping jaws 122 and 124 are adapted to be rigidly attached to proximal ends 114 and 116 of rotatable levers 110 and 112 of conventional vascular clamps (FIGS. 6, 8).

Figure 9:
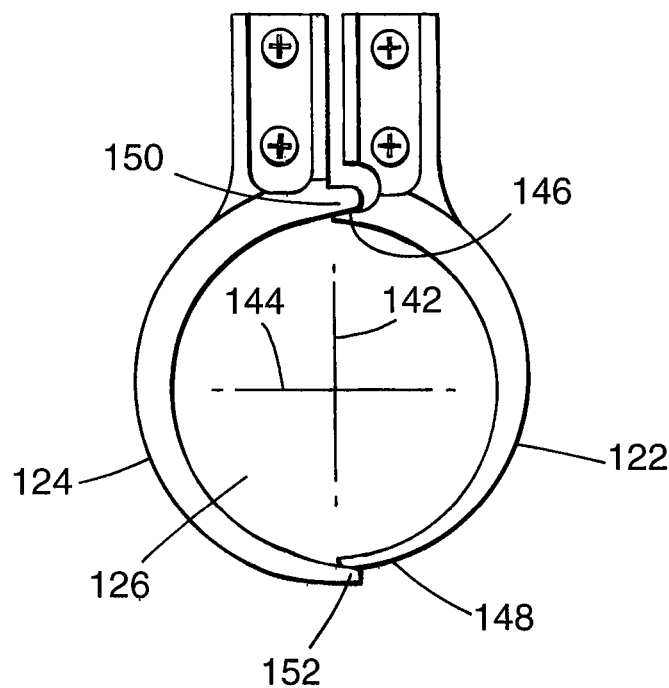
Figure 10:
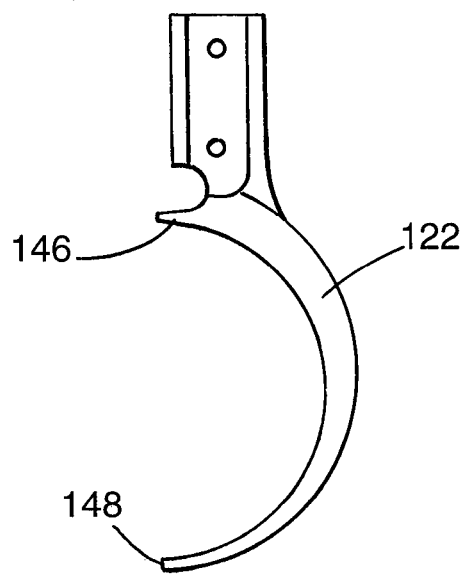
FIGS. 10, 11 show two views of a male clamping jaw.
Figure 11:
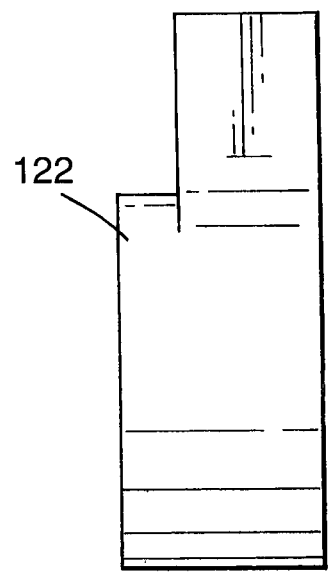

The suggested supplementary vascular clamp 100 comprises also a compensating means for correcting irregularity in thickness of aorta walls (FIG. 6). This compensating means contains clamping jaws 122, 124 with concave semi-oval inner surfaces 134, 136. Clamping jaws 122, 124 are movable between open position and closed position (FIGS. 8, 6). They define in closed position a through oval cavity 126 with the long axis of symmetry 142 coinciding with the parting plane of these clamping jaws 122, 124, and the short axis of symmetry 144 perpendicular to this parting plane (FIG. 9).

Vascular clamp 100 further includes a first tightening means for providing secure enclosure of aorta walls containing clamping jaws 122, 124 (FIG. 9) shaped as concave semi-oval cavities and overlapping one another. These clamping jaws 122, 124 overlap one another by their ends in such a way that ends 146, 148 of one of the clamping jaws, in this case clamping jaw 122, are male, and ends 150, 152 of the other of clamping jaws, in this case clamping jaw 124—female (FIG. 9).

Figure 12:
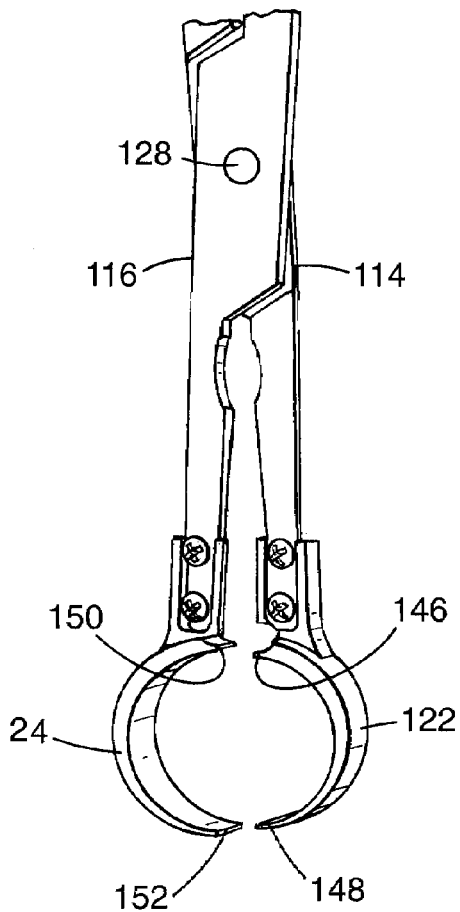
FIGS. 12, 13 show the working part of the suggested vascular clamp in partly open and in open positions.

The second tightening means for secure enclosure of aorta walls contains clamping jaws 122, 124 shaped as semi-oval cavities, the ends whereof 146, 148 and 150, 152 respectively, facing and overlapping one another are flexible (FIG. 12).

Figure 13:
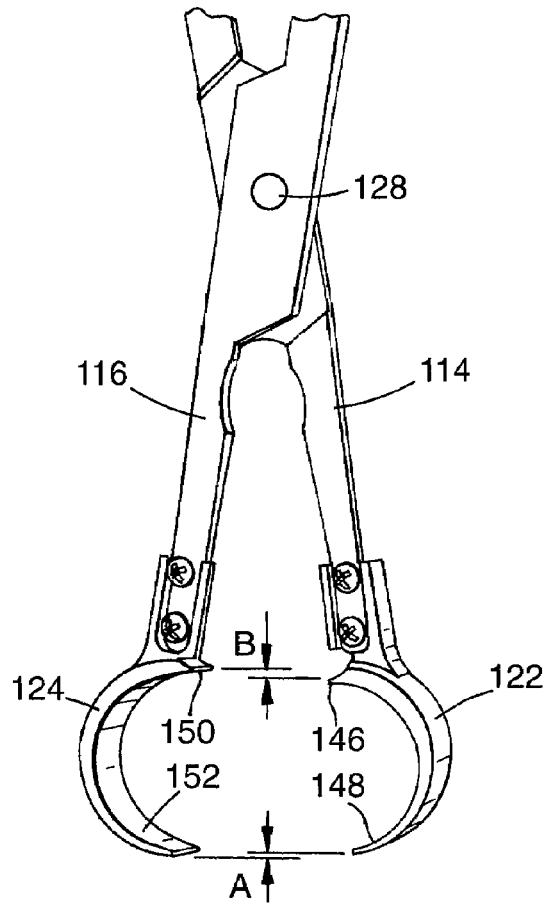
Figure 14:
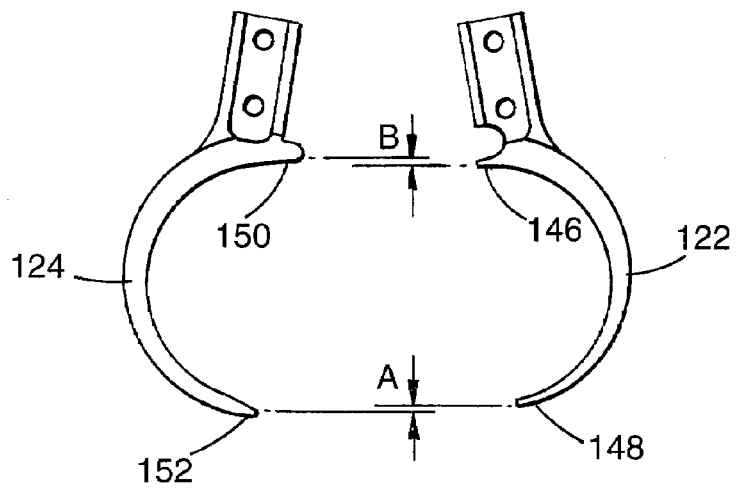
FIG. 14 shows a diagram of the working part of the suggested vascular clamp in open position.

Vascular clamp 100 is also provided with a means for providing regular ejection of staples over the whole inner surface of prosthesis connection with the aorta. This means is a clearance between the ends of clamping jaws 122, 124. The ends of clamping jaws 122 and 124 facing and overlapping one another, 146 and 150, 148 and 152 respectively, are disposed with clearances A and B between them (FIG. 13). These clearances A and B may be of 0.3 mm (FIG. 14).

The claimed device according to the third embodiment operates as follows.

In a surgical operation, the aorta or some other blood vessel is exposed. Within this blood vessel there is inserted a prosthesis, such as a graft or stent-graft, and a means for securing this prosthesis to the blood vessel wall, such as an open approach stapler. Then a supplementary vascular clamp 100 is applied onto the outer surface of this blood vessel. At the moment of applying vascular clamp 100 its proximal ends 114 and 116 with clamping jaws 122 and 124 are located on both sides of the operated blood vessel, whereupon, due to forces applied to distal handle ends 118 and 120, levers 110 and 112 turn about pin 128 to bring together clamping jaws 122 and 124. Clamping jaws 122 and 124 define in their closed position a through cylindrical cavity 126 enclosing the blood vessel. Every effort is made to position supplementary vascular clamp 100 in such a way that it should be located by its clamping jaws 122 and 124 concentrically on the actuator of open approach stapler in the area of ejecting its staples. Then the position of clamp 100 is fixated by fixing grips 130 and 132, selecting such a position of their mutual connection which provides sufficiently tight occlusion of the outer surface of blood vessel by clamping jaws 122 and 124.

Then the open approach stapler is actuated to suture by staples the prosthesis to the inner surface of a blood vessel (not shown in the drawings). At the moment of the open approach stapler operation the first and second tightening means of supplementary vascular clamp 100 containing flexible mutually overlapping ends 146 and 150, 148 and 152 of clamping jaws 122 and 124 tightly enclose the blood vessel outer surface to prevent it from injuries and simultaneously provide the assigned bending of staple ends of the stapler. The compensating means shaped as an oval cavity 126 provides correction of irregularity in the thickness of walls of the operated blood vessel, in particular the aorta, which is achieved by redistribution of the aorta over the entire oval section 126 of clamp 100.

The claimed supplementary vascular clamp is developed as a device comprised in the tool kit for an open approach stapler. At the same time this clamp may be used for work with other endovascular staplers. The suggested clamp may be as well used for work with other tools applied in particular for cavitary operations, such as operations on the bowels.

While this invention has been described in conjunction with specific embodiment thereof, it is evident that many alternatives, modifications and variations will be apparent to those skilled in the art. Accordingly, the preferred embodiments of the invention as set forth herein are intended to be illustrative, not limiting. Various changes may be made without departing from the spirit and scope of the invention as defined in the following claims.

The invention claimed is:

1. A support clamp for a stapler used during connecting a prosthesis to a vessel by staples, said clamp comprising:
    a) a pair of pivoting levers each of them having a proximal end and a distal handle end, each of the pivoting levers is provided with a C-shaped clamping jaw associated with a corresponding proximal end, wherein, during pivoting of the levers their clamping jaws are displaceable between an open position and a closed position, such that the vessel can be respectively released or embraced by the clamping jaws without occluding the vessel;
    b) a tightening means for providing a tight contact between the clamping jaws and an outer surface of the vessel and abutting the vessel towards the stapler to enable bending of a staple end during connecting the prosthesis to an inner surface of the vessel;
    c) a fastener means for attaching the tightening means to a corresponding clamping jaw, and
    d) a compensating means for compensating irregularity in thickness of the walls of the vessel.

2. A clamp according to claim 1,
wherein said levers are provided with a locking means to secure the levers in a position.

3. A clamp according to claim 1,
wherein said compensating means is configured as a protrusion made on one of the clamping jaws and a corresponding depression made on a second clamping jaw.

4. A clamp according to claim 1,
wherein each of the clamping jaws is provided with a concave inner surface and an outer surface, which is substantially parallel to the inner surface.

5. A clamp according to claim 1,
wherein the clamping jaws are releasably attached to the pivoting levers of a conventional vascular clamp.

6. A clamp according to claim 1, wherein the tightening means is configured as pads made of a resilient material, each pad being attached to a corresponding inner surface of a corresponding clamping jaw.

7. A supplementary vascular clamp according to claim 1, wherein said tightening means for providing intra-aortal bending of staple ends of the open approach stapler and secure enclosure of aorta walls by the clamping jaws contains at least one strip from resilient material, substantially rubber or plastic, which is attached by each of its ends to the inner semi-cylindrical surface of a corresponding clamping jaw.

8. A supplementary vascular clamp according to claim 7, wherein said tightening means for providing intra-aortal bending of staple ends of the open approach stapler and secure enclosure of aorta walls by the clamping jaws, containing at least one strip from resilient material substantially rubber or plastic, is configured to adjust the force of occlusion of a blood vessel outer surface.

9. A supplementary vascular clamp according to claim 8, wherein said tightening means for providing intra-aortal bending of staple ends of the open approach stapler and secure enclosure of aorta walls by the clamping jaws containing at least one strip from resilient material, substantially plastic, is configured to adjust the force of occlusion of a blood vessel outer surface via a mechanism for tensioning said strip.

10. A supplementary vascular clamp according to claim 1, wherein said compensating means for correcting irregularity in thickness of aorta walls substantially contains a ridge at the free end of one of the clamping jaws and a valley opposite to this ridge at a corresponding free end of the other clamping jaw.

* * * * *